United States Patent
Karls et al.

(10) Patent No.: US 9,325,107 B2
(45) Date of Patent: Apr. 26, 2016

(54) ELECTRICAL CONNECTOR ASSEMBLY FOR NEURAL MONITORING DEVICE AND METHOD OF USING SAME

(71) Applicant: Neuralynx, Inc., Bozeman, MT (US)

(72) Inventors: Phillip Karls, Belgrade, MT (US); Shawn Olson, Bozeman, MT (US)

(73) Assignee: Neuralynx, Inc., Bozeman, MT (US)

( * ) Notice: Subject to any disclaimer, the term of this patent is extended or adjusted under 35 U.S.C. 154(b) by 35 days.

(21) Appl. No.: 14/507,130

(22) Filed: Oct. 6, 2014

(65) Prior Publication Data

US 2015/0111399 A1 Apr. 23, 2015

Related U.S. Application Data

(60) Provisional application No. 61/892,083, filed on Oct. 17, 2013.

(51) Int. Cl.
*H01R 13/60* (2006.01)
*H01R 13/62* (2006.01)
*H01R 12/73* (2011.01)
*A61B 5/04* (2006.01)
*A61B 5/00* (2006.01)

(52) U.S. Cl.
CPC ........ *H01R 13/6205* (2013.01); *A61B 5/04001* (2013.01); *H01R 12/73* (2013.01); *A61B 5/6814* (2013.01); *A61B 5/6882* (2013.01); *H01R 2201/12* (2013.01)

(58) Field of Classification Search
None
See application file for complete search history.

(56) References Cited

U.S. PATENT DOCUMENTS

| | | | |
|---|---|---|---|
| 4,004,298 A | 1/1977 | Freed | |
| 4,025,964 A | 5/1977 | Owens | |
| 4,067,342 A | 1/1978 | Burton | |
| 4,112,941 A | 9/1978 | Larimore | |
| 4,211,456 A | 7/1980 | Sears | |
| 4,259,965 A | 4/1981 | Fukuda et al. | |
| 4,653,503 A | 3/1987 | Heath | |
| 4,947,846 A | 8/1990 | Kitagawa et al. | |
| 6,565,363 B2 * | 5/2003 | Downing ........... | H01R 13/6205 439/38 |
| 7,344,380 B2 * | 3/2008 | Neidlein ............ | H01R 13/6205 439/374 |
| 7,359,744 B2 | 4/2008 | Lee et al. | |
| 7,410,364 B2 * | 8/2008 | Kishi ................... | H01R 12/716 439/566 |
| 7,473,145 B2 | 1/2009 | Ehr et al. | |
| 7,668,580 B2 | 2/2010 | Shin et al. | |
| 7,677,903 B1 * | 3/2010 | Huang ................. | H01R 13/112 439/64 |
| 7,722,412 B2 | 5/2010 | Ehr et al. | |
| 8,214,009 B2 | 7/2012 | Shin et al. | |
| 8,332,009 B2 | 12/2012 | McLaughlin et al. | |
| 8,388,353 B2 | 3/2013 | Kiani et al. | |

(Continued)

*Primary Examiner* — Xuong Chung Trans
(74) *Attorney, Agent, or Firm* — Antoinette M. Tease

(57) ABSTRACT

An electrical connector assembly comprising an electrode interface board with a socket portion of a subminiature dual-row electrical connector attached to the top surface of a first printed circuit board and a first plurality of magnets attached to the bottom surface. The socket portion comprises a plastic housing and a plurality of female contacts with protruding contact points. The connector assembly further comprises a head stage with a top socket, connector and a second printed circuit board. A plug portion of the electrical connector is attached to the bottom surface of the second printed circuit board and a second plurality of magnets is attached to the bottom surface. The plug portion comprises a plastic housing and a plurality of male contacts with detents. The male contacts mate with the female contacts so that the protruding contact point of each female contact touches an inside distal surface of a male contact.

6 Claims, 8 Drawing Sheets

(56) References Cited

U.S. PATENT DOCUMENTS

| | | |
|---|---|---|
| 8,408,948 B2 | 4/2013 | Selvitelli et al. |
| 8,979,551 B2 * | 3/2015 | Mongold ............... H01R 12/73 439/74 |
| 9,124,011 B2 * | 9/2015 | Miyazaki ............. H01R 12/716 |
| 2005/0154273 A1 | 7/2005 | Lee et al. |
| 2007/0093705 A1 | 4/2007 | Shin et al. |
| 2008/0033276 A1 | 2/2008 | Ehr et al. |
| 2008/0050984 A1 | 2/2008 | Ehr et al. |
| 2010/0049028 A1 | 2/2010 | Shin et al. |
| 2010/0160762 A1 | 6/2010 | McLaughlin et al. |
| 2010/0233889 A1 | 9/2010 | Kiani et al. |
| 2012/0196474 A1 | 8/2012 | Selvitelli et al. |

* cited by examiner

ELECTRICAL CONNECTOR ASSEMBLY FOR NEURAL MONITORING DEVICE AND METHOD OF USING SAME

CROSS-REFERENCE TO RELATED APPLICATION

This application claims priority to U.S patent application Ser. No. 61/892,083 filed on Oct. 17, 2013. The contents of the '083 application are incorporated herein by reference as if fully set forth herein.

BACKGROUND OF THE INVENTION

1. Field of the Invention

The present invention relates to the field of medical research devices, and more particularly, to a magnetically aligned electrical connector assembly for use with a neural monitoring device in experiments on live animals.

2. Description of the Related Art

There are numerous examples of electrical connectors that employ magnetic components to assist in the alignment or attachment of electrical connections that are the subject of issued patents, but none of these inventions includes the novel features and advantages of the connector of the present invention. The present invention provides for an easy and reliable connection to be made between the two halves of a subminiature, high-density surface-mount connector by persons having very little prior training. The user is not required to make an accurate visual alignment of the electrical pins during the connection process because magnetic force provides precise alignment of the pins when the user brings the two halves of the connector into approximately alignment.

U.S. Pat. No. 4,004,298 (Freed, 1977) discloses a magnetically aligned connector for a heart-assist apparatus, wherein the separation force to disconnect the two halves of the connector is less than the pulling force that will cause injury to the patient. In a preferred embodiment, the connector is used to connect one electrical signal and one source of compressed air. Although magnets are used to obtain proper alignment of the two connector halves during the connection procedure, a mechanical interlock is used to positively lock the two parts together during use. The magnets, which are in direct contact, serve as the electrical contacts. In one embodiment (FIG. 2), three magnets in the top half align with three magnets in the bottom half, with magnet polarization set so as to cause the two halves to align in only one orientation.

U.S. Pat. No. 4,025,964 (Owens, 1977) discloses an electrical connector for connecting wires within the body of a human medical patient to external wiring. The connector is comprised of a socket and a complimentary shaped plug. The plug is held in the socket by the magnetic force between a magnet located in the socket and magnetic material located in the plug. The electrical contacts consist of inclined conductive strips on the plug assembly that wedge against mating inclined conductive strips on the socket assembly. The device is described as being suitable for connecting two or three different conductor wires.

U.S. Pat. No. 4,067,342 (Burton, 1978) discloses a flexible electrode device capable of transmitting electrical signals through human skin. The device is comprised of flexible, electrically conductive adhesive tape. External wires are connected to the tape via magnetic particles on the wire connector that magnetically couple with magnetic particles bonded to the tape. The magnetic particles, which are in direct contact, serve as the electrical contacts.

U.S. Pat. No. 4,112,941 (Larimore, 1978) discloses a biomedical electrode for providing a removable and rotatable electrical connection to the skin of a medical patient. The device consists of an electrode component attached to the skin and a connector component with external wires. Magnetic force is used to hold the electrode and connector components in electrical contact. The electrode component comprises a magnetic plate and a raised post. The connector component comprises a magnetic ring with a center hole. When the two components are held together by magnetic force, the post of the electrode fits into the specially shaped hole of the connector, so that the post and the inside walls of the hole are always in electrical contact. The device comprises a single electrical conductor.

U.S. Pat. No, 4,211,456 (Sears, 1980) discloses a magnetically connected electrical connector, wherein the connector component of the device comprises a spherically shaped ferrous metal male connector that attaches to a female component via magnetic force provided by a permanent magnet located within the female component. The device provides a single electrical connection for each male-female pair of components.

U.S. Pat. No. 4,259,065 (Fukuda et. al., 1981) discloses an electrode device for connecting electrical monitoring equipment to the skin of a medical patient. The device comprises a base component that attaches to the skin of a medical patient and a terminal component that may be removably attached to the base component by magnetic force. The terminal component comprises a disc-shaped magnet that attaches magnetically to a disc-shaped ferro-magnetic element within the base unit. The electrical contacts are the magnet and the ferromagnetic material. The device provides a single electrical connection for each magnet-ferro magnetic material pair.

U.S. Pat. No. 4,653,503 (Heath, 1987) discloses a physiological electrode that is designed to be attached to the body of a medical patient. The device comprises a magnetic coupler that removably attaches a lead wire assembly to the electrode assembly, which is mounted on the patient's skin. The lead wire assembly comprises a permanent magnet, and the electrode assembly comprises a matching ferro-magnetic member, which is attracted by magnetic force to the magnet, thereby holding the lead wire assembly in contact with the electrode assembly. In this device, the electrical contacts are provided by the magnet and ferro-magnetic material, and there is a single electrical connection for each magnet-ferro magnetic material pair. The electrode assembly may optionally comprise a raised lip to help prevent accidental release of the lead wire assembly.

U.S. Pat. No. 4,947,846 (Kitagawa et al., 1990) discloses a waterproof electrode device that is designed to be attached to the skin of a medical patient. The device comprises an electrode component that attaches to a medical patent's skin and a removable wire lead connector that is magnetically attached to the electrode component. The magnetic attachment force is provided by a permanent magnet within either the electrode component or the connector component and either a magnet or magnetic material within the other component. The electrical connection is made waterproof by a closed-cell foam seal between the two components. The electrical contacts are provided by a conductive yoke in the connector component that contacts the magnetic material of the electrode component. This device provides a single electrical connection for each magnet-magnet pair or magnet-magnetic material pair.

U.S. Pat. No. 7,359,744 (Lee et. al., 2008) discloses an electrical bio-potential sensor (electrode) that connects to a medical patient's skin via short needles that penetrate into the upper layer of skin. Electrical signals from the needles are conducted via electrical contacts to a removable wireless transmitter that is mounted on top of the electrode component. The electrical contacts on the electrode component and transmitter component are held together by magnetic force that is provided by a plurality of magnets on the electrode component that attach to a plurality of matching magnets that are mounted on the transmitter component. The details of the electrical contacts are not disclosed. The example device described in the patent document comprised four magnet pairs and three electrical connections.

U.S. Pat. No. 7,473,145 (Ehr et al., 2009) and U.S. Pat. No. 7,772,412 (Ehr et. al., 2010) disclose several embodiments of a removable and reusable electrode connector component. In some embodiments (shown in FIGS. 7 through 10), the connector wire is attached to a flat, electrically conductive magnet, and this magnet attaches to a magnetic electrode pad having an electrically conductive zone that provides an electrical connection from the electrode to the connector wire. These devices comprise one electrical connector for each magnet pair.

U.S. Pat. No. 7,068,580 (Shin et al., 2010) and U.S. Pat. No. 8,214,009 (Shin et al., 2012) disclose several embodiments of an electrode and an analog-to-digital signal processing member. In one embodiment (FIG. 11), the electrical contacts of the electrode component and the signal processing unit may alternately be "mechanically combined with each other using magnetism and a magnetic substance." No further details of the magnetic components are disclosed.

U.S. Pat. No. 8,332,009 (McLaughlin et al., 2012) discloses a two-part sensor unit for medical patents comprising a sensing component mounted on the patient's skin and a receiving component that transmits the signals wirelessly. The two components are electrically and magnetically connected by a connector unit that comprises a magnet stud and a magnetizable stud, with a magnetic female clip in between the two studs. The device comprises one magnet assembly for each electrical conductor.

U.S. Pat. No. 8,388,353 (Kiani et al., 2013) discloses a magnetic connector comprising a receptacle component and a plug component. FIG. 5B shows a 42-contact connector. In some embodiments, an electromagnet is used to provide magnetic force to join the two components, thereby causing electrical contact between an array of electrical pins and sockets in the two components. In other embodiments, a permanent magnet is used to provide magnetic force that pulls the two components together, while actuating an electromagnet overcomes the attractive force of the permanent magnet and pushes the two components apart. The device comprises an array of electrical contacts and a single permanent magnet for embodiments that incorporate a permanent magnet. There is no other detail disclosed regarding alignment.

U.S. Pat. No. 8,408,948 (Selvitelli et al., 2013) discloses several embodiments of electrocardiograph (ECG) electrode connectors. These devices comprise a spring member as a component of the mechanical locking mechanism of the various embodiments, wherein the locking mechanisms use cams or other methods to firmly and removably grasp an electrode wire. Although magnets are not depicted or specifically described in the various embodiments, the description (column 3, lines 50-55) states: "It should be understood that the spring members disclosed herein are not limited to coil and/or leaf springs, and may include any suitable source of biasing force, including without limitation gas springs, pressure- or vacuum-actuated devices, elastomeric springs, magnetic or electromagnetic devices . . . "

U.S. Pat. No. 3,786,391 (Mathhauser, 1974) discloses a magnetic self-aligning electrical connector. This device comprises a nominally round male coupling half and a nominally round female coupling half, with a plurality of male electrical connectors mounted around a central magnet in the male half, and a matching plurality of female electrical connectors mounted around a central piece of ferro-magnetic material. The male connectors are cylindrical with tapered points, and the female sockets are cylindrical with tapered bottoms. When the two halves of the device are placed in close proximity, the attractive magnetic force between the magnet and the ferro-magnetic material causes the male pins to seat into the female sockets, with the tapered portions of the pins and sockets making electrical contact. The description does not specifically state if the magnet and ferro-magnetic material are in direct contact when the two halves of the device are electrically connected.

BRIEF SUMMARY OF THE INVENTION

The present invention is an electrical connector assembly for a neural monitoring device, the electrical connector assembly comprising: an electrode interface board comprising a first printed circuit board with a top surface and a bottom surface, wherein a socket portion of a subminiature dual-row electrical connector is attached to the top surface of the first printed circuit board, wherein a first plurality of magnets is attached to the bottom surface of the first printed circuit board, and wherein the socket portion comprises a plastic housing and a plurality of female contacts, each female contact comprising a protruding contact point; a head stage comprising a top socket connector and a second printed circuit board with a top surface and a bottom surface, wherein a plug portion of a subminiature dual-row electrical connector is attached to the bottom surface of the second printed circuit board, wherein, a second plurality of magnets is attached to the bottom surface of the second printed circuit board, wherein each magnet has a height, wherein the height of all of the magnets in the second plurality of magnets is the same, wherein the plug portion comprises a plastic housing and a plurality of male contacts, each male contact comprising a detent, and wherein each of the male contacts in the plurality of male contacts is electrically connected to the top socket connector via a through-board connection; wherein the male contacts of the plug portion mate with the female contacts of the socket portion so that the protruding contact point of each female contact touches an inside distal surface of a male contact and wherein the height of the magnets in the second plurality of magnets prevents the male contacts from seating further into the female contacts.

In a preferred embodiment, the protruding contact point of each of the female contacts in the plurality of female contacts does not engage with the detent of the male contact but stops short of the detent as a result of the configuration and height of the magnets in the second plurality of magnets. Preferably, the magnets in the first plurality of magnets and the magnets in the second plurality of magnets are configured so as to cause the male contacts of the plug portion of the head stage to align precisely over the female contacts of the socket portion of the electrode interface board when the head stage and electrode interface board are brought into approximate alignment. Preferably, the magnets in the first plurality of magnets and the magnets in the second plurality of magnets are configured so as to cause the electrode interface board and the head stage to be magnetically repelled if they are brought into reverse alignment. The female contacts are preferably recessed into the plastic housing of the socket portion.

The present invention is also a method for attaching an electrode interface board to a head stage of a neural monitoring device for use in experiments on live animals, the method comprising the steps of: wherein tire electrode interface board comprises a first printed circuit board with a top surface and a bottom surface, attaching a socket portion of a subminiature dual-row electrical connector to the top surface of the first printed circuit board, the socket portion comprising a plurality of female contacts, and attaching a first plurality of magnets to the bottom surface of the first printed circuit board; wherein the head stage comprises a second printed circuit board with a bottom surface, attaching a plug portion of a subminiature dual-row electrical connector to the bottom surface of the second printed circuit board, the plug portion comprising a plurality of male contacts, and attaching a second plurality of magnets to the bottom surface of the second printed circuit board, each magnet in the second plurality of magnets having a bottom surface; using the first plurality of magnets and the second plurality of magnets to align the female contacts with the male contacts to create a gap of roughly 0.2 millimeters between the bottom surface of each magnet in the second plurality of magnets and the top surface of the first printed circuit board; and closing the gap between the bottom surface of each magnet in the second plurality of magnets and the top surface of the first printed circuit board by manually pressing the male contacts into the female contacts until the bottom surface of the magnets in the second plurality of magnets comes into contact with the top surface of the printed circuit board.

REFERENCE NUMBERS

Figure 1:
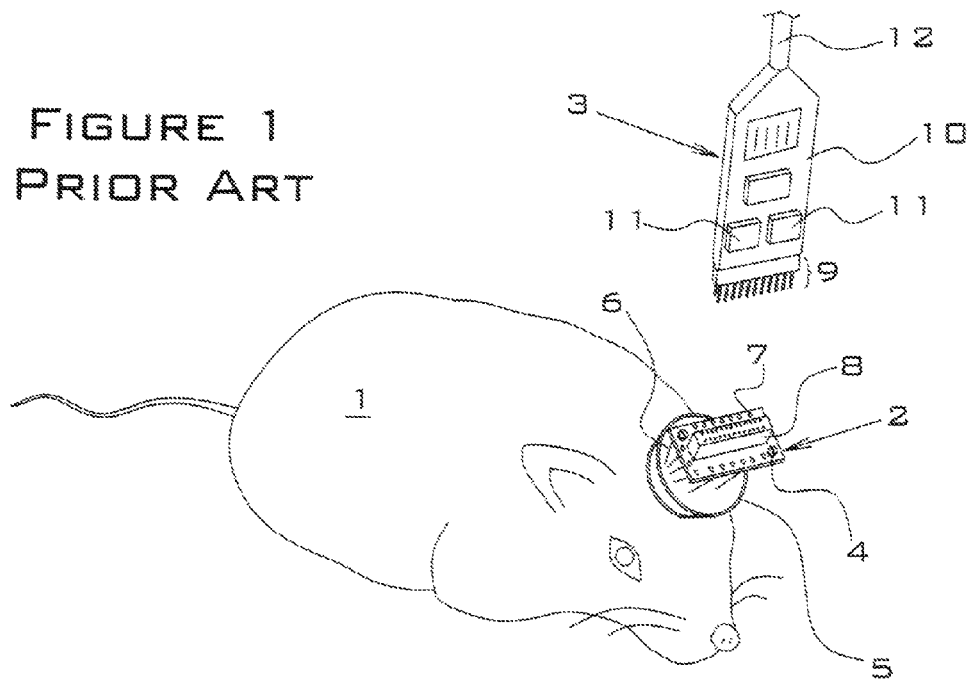
FIG. 1 is a perspective view of the prior art with the two halves of the device's electrical connector shown in a separated and electrically disconnected position.

1 Laboratory rat
2 Electrode interface board, EIB (prior art)
3 Head stage (prior art)
4 Screw
5 Implanted electrode harness
6 Electrode wire
7 Solder hole
8 Top socket connector (prior art)
9 Top pin connector (prior art)
10 Circuit board of head stage (prior art)
11 Analog signal processing integrated circuit chip
12 Instrument cable (prior art)
13 Electrode interface board, EIB
14 Head stage
15 Socket portion of subminiature dual-row connector, socket
16 Circuit board of EIB
17 Circuit board of head stage
18 Analog-to-digital integrated circuit chip
19 Top socket connector
20 Monitoring instrument connector plug
21 Monitoring instrument electrical cable
22 Magnet, head-stage
23 Magnet, EIB
24 Plug portion of subminiature dual-row connector, plug
25 Plastic housing of socket portion of subminiature connector
26 Female electrical contact of socket portion of subminiature connector
27 Contact point of female electrical contact
28 Circuit board conductor
20 Plastic housing of plug portion of subminiature connector
30 Male electrical contact of plug portion of subminiature connector
31 Detent in male electrical contact
32 Through-board electrical connection
33 Gap
34 Upper circuit board assembly (prior art)
35 Top circuit board (prior art)
36 Lower circuit board assembly (prior art)
37 Bottom circuit board (prior art)

DETAILED DESCRIPTION OF INVENTION

The present invention is an electrical connector assembly for use in connection with an electronic device that collects and processes neural voltages that are obtained from electrodes implanted into the brain of an animal such as a laboratory rat. The invention composes two major components, namely, an electrode interface board (EIB) and a head stage. Typically, the EIB is permanently attached to the top of the head of the animal and incorporates a passive electrical connector with a separate contact for each electrode wire. The head stage contains electronic signal processing components and transmits the processed neural voltages to a monitoring and recording instrument. The head stage is connected to the EIB when data are being collected and disconnected between experiments. The present invention comprises a novel electrical connector assembly that connects the individual electrode signals from the EIB to the head stage when these two components are connected. The electrical connector of the present invention comprises a plug section that is mounted on the head stage and a mating socket section that is mounted on the EIB. The EIB and head stage each contains four permanent magnets that are installed so as to draw the plug and socket sections together and to precisely align them with magnetic attraction. This allows the multiple male contacts of the plug section to be easily and correctly inserted into the corresponding multiple female contacts of the socket section, using minimal manual force and with no precise visual alignment required. The magnets are installed so that the EIB and head stage are magnetically repelled if the two parts are accidently brought into reverse alignment.

The connection procedure is accomplished in two sequential steps. In step 1, the user manually brings the head stage and the EIB into approximate alignment, at which time magnetic attraction between the two components causes the male electrical contacts of the plug section in the head stage to align precisely over the female electrical contacts of the socket connector in the EIB. In step 2, the user applies manual compressive force to the EIB-head stage assembly, and the combination of manual force and magnetic attraction causes the plug and socket components of the electrical connector to snap together with a "click" that can be both heard and felt by the user, thereby confirming that a correct connection has been made.

The plug and socket connector components of the present invention are preferably two halves of a commercially available device, namely, a subminiature, surface-mount, dual-row connector. For prior art applications that utilize this preferred connector, the female electrical contacts of the socket mechanically lock into detents manufactured into the male electrical contacts of the plug, thereby preventing the connector from accidental disconnection when the connector is subjected to external forces. In contrast to these prior art applications of the subminiature connector, the present invention is designed so that the female contacts do not snap into the detents of the male contacts to lock the connection, but instead, the contacts are prevented from accidental disconnection by magnetic attractive force in combination with sliding friction of the touching (but not locked together) male and female contacts.

In the present invention, the elimination of the requirement for precise visual alignment of the miniature electrical contacts provides several advantages over the prior art. First, it reduces the chance of expensive pin damage and resulting down time caused by user error. Second, it allows less highly-skilled workers to be employed for making the electrical connections to the lab animal. Third, it allows the electronic circuitry to be positioned closer to and parallel to the top of the animal's head, thereby reducing the potential for damage to the implant.

Physically connecting and disconnecting the head stage and the EIB of the present invention requires significantly less mechanical energy than is required when connecting the head stage and EIB of the prior art. First, the connection process results in downward force on the top of the head of the laboratory animal, which can damage the implant and cause trauma to the animal. Reducing the connection energy causes a corresponding reduction in force to the top of the animal's head and is, therefore, beneficial. Second, the laboratory animal may occasionally exert enough pulling or twisting force to cause damage to the implant unless the head stage disconnects from the EIB. Minimizing the energy required to automatically disconnect the head stage from the EIB during the occurrence of potentially damaging forces can eliminate damage caused by these forces.

The details of the present invention are described in greater detail in reference to the following figures.

Figure 2:
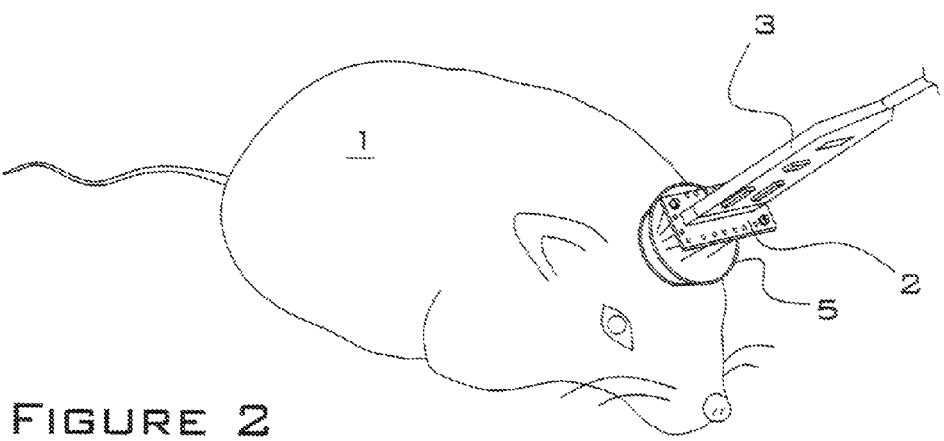
FIG. 2 is a perspective view of the prior art with the two halves of the device's connector shown in an electrically connected position and mounted on the head of a laboratory rat.

FIGS. 1 and 2 illustrate an example of the prior art being used for neural research on a laboratory rat 1. This prior art is an example of an analog neural monitoring device manufactured by Neuralynx, Inc of Bozeman, Mont. FIG. 1 is a perspective view of the prior art with the two halves of the device's electrical connector shown in a separated and electrically disconnected position. The major components of the prior art consist of an EIB 2 and a head stage 3. The EIB 2 is attached with screws 4 to an implanted electrode harness 5 that is attached to the skull of the rat 1. A plurality of electrode wires 6 extends from zones within the rat's brain to solder holes 7 in the EIB; these wires are connected to individual electrical connector sockets in a top socket connector 8. The prior art head stage 3 comprises a top pin connector 9, a circuit board 10, analog signal processing integrated chips 11, and an instrument cable 12, whose proximal end is attached to the circuit board 10. The top pin connector 9 of the head stage 3 connects to the top socket connection 8 of the EIB 2. A monitoring and recording instrument (not shown) attached to the distal end of the instrument cable 12.

FIG. 2 is a perspective view of the prior art with the two halves of the device's connector shown in an electrically connected position and mounted on the head of a laboratory rat 1. As shown, when the head stage 3 is connected to the EIB 2, the head stage 3 projects in a substantially perpendicular direction from the top of the head of the rat 1. In normal practice, the EIB 2 is permanently attached to the rat 1, and the head stage 2 is connected for an experiment and then disconnected between experiments. For this reason, a quick and easy method of connecting and disconnecting the head stage 3 from the EIB 2 that causes minimum trauma to the animal is advantageous. In addition, in order to minimize accidental damage to the implanted electrode wires, it is advantageous to minimize the weight of the EIB 2 and the head stage 3 and to position these components as near to the top of the head of the rat 1 as possible. It is also advantageous to minimize the mechanical energy required to connect and disconnect the head stage and EIB in order to lessen trauma to the animal and damage to the implant.

Figure 3:
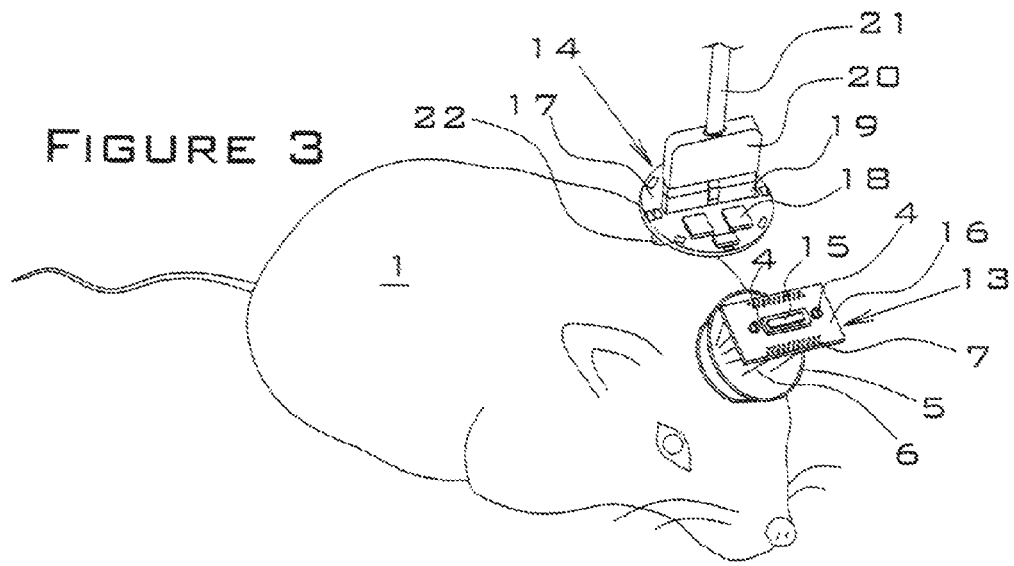
FIG. 3 is a perspective view showing the two halves of the present invention in a separated position, prior to being electrically connected.
Figure 4:
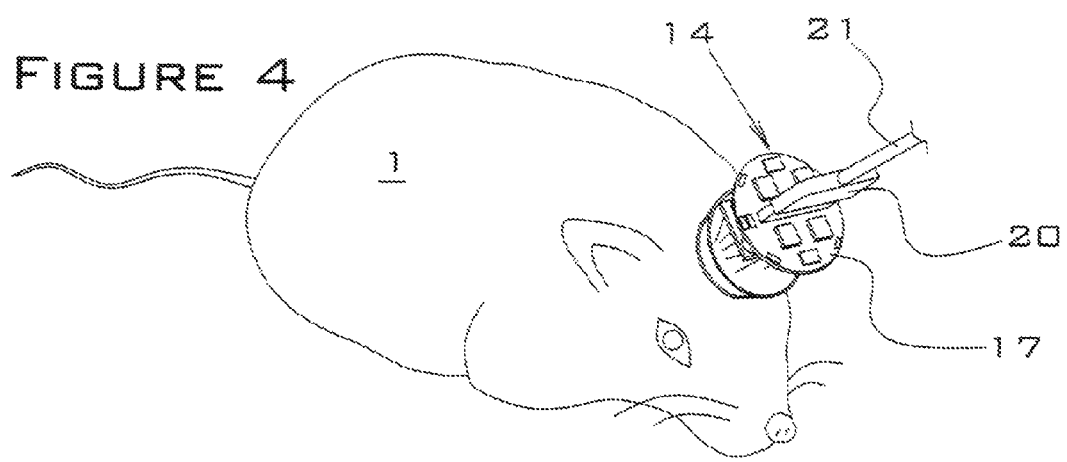
FIG. 4 is a perspective view of the present invention assembled and attached to the head of a laboratory rat.

FIGS. 3 and 4 illustrate the present invention being used for neural research on a laboratory rat 1. FIG. 3 is a perspective view showing the two halves of the present invention in a separated position, prior to being electrically connected. As shown in FIG. 3, the major components of the present invention consist of an EIB 13 and digital output head stage 14. The EIB 13 is attached to the rat 1 with screws 4 to an implanted electrode harness 5 that is attached to the skull of the rat 1. A plurality of electrode wires 6 extends from zones within the rat's brain to solder holes 7 in the EIB. These solder holes 7 are connected to individual electrical connector sockets in a socket portion 15 of a subminiature dual-row connector. The socket 15 is mounted on a circuit board 16 of the EIB 13.

The head stage 14 comprises a surface-mount printed circuit board 17, analog-to-digital integrated circuit chips 18, and a top socket connector 19. The top side of the top socket connector 19 attaches to a monitoring instrument connector plug 20, which is connected to a monitoring instrument electrical cable 21. The bottom side of the socket connector 19 is electrically connected to the plug portion of a miniature dual-row connector (shown in following FIG. 6 through 9) that is mounted on the bottom side of the circuit board 17. One of the four head-stage magnets 22 that is attached to the bottom of the circuit board 17 of the head stage 17 is shown in FIG. 3.

Figure 6:
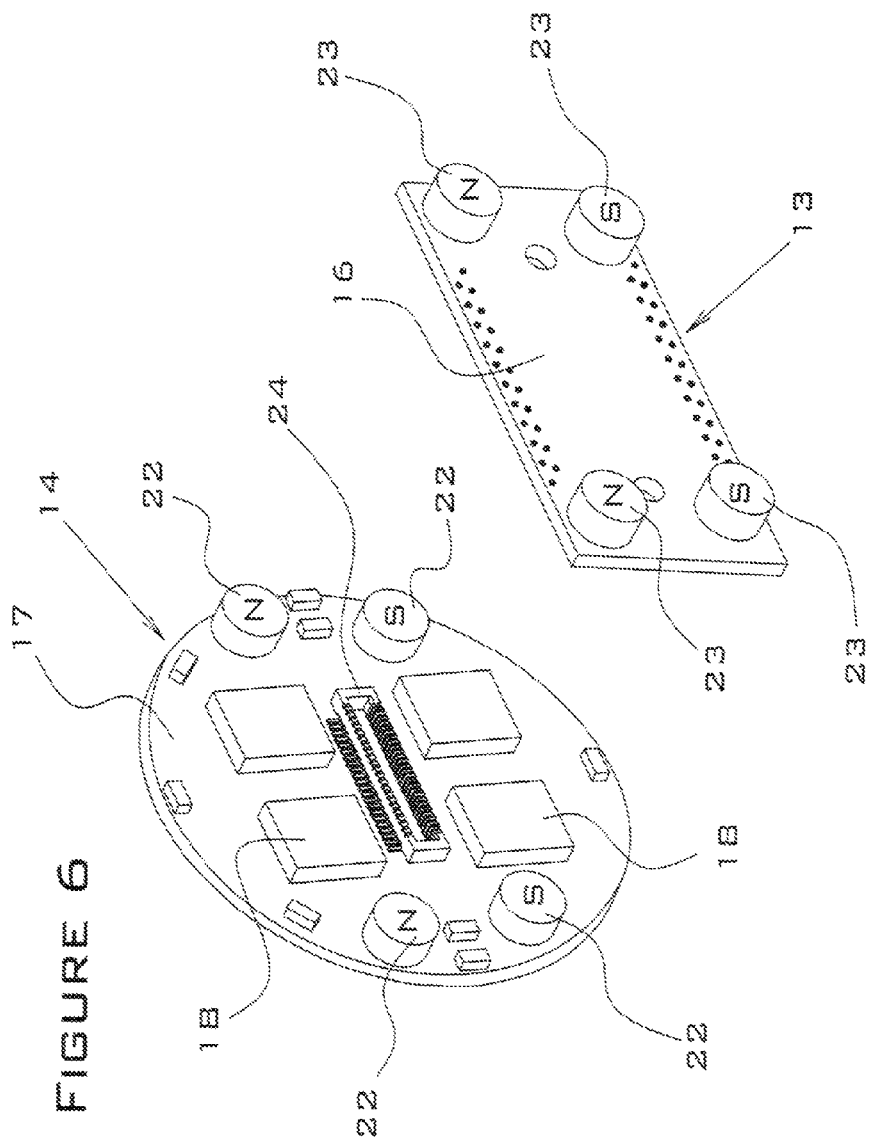
FIG. 6 is a magnified perspective view of the bottom sides of the EIB and the head stage of the present invention, shown disconnected.

The four head-stage magnets 22 and the four EIB magnets are described in detail in reference to the following FIG. 6.

FIG. 4 is a perspective view of the present invention assembled and attached to the head of the rat 1. As shown in FIG. 4, the circuit board 17 of the head stage 14 is positioned substantially parallel to the top of the head of the rat 1, whereas the circuit board 10 of the head stage 3 of the prior art (shown in FIG. 2) is positioned substantially perpendicular to the top of the head of the rat 1. Because of this difference, the center of mass of the head stage 14 of the present invention is positioned closer to the head of the rat 1 than the center of mass of the head stage 3 of the prior art; therefore, the moment arm of the present invention on the implanted electrode harness 5 is less than in the prior art.

Referring again to FIG. 2, it is necessary to position the circuit board 3 of the prior art perpendicular to the head of the rat 1 so that the top pin connector 9 can be visually aligned with the top socket connector 8 when these two components are being connected. By contrast, because the connector components of the present invention are magnetically aligned rather than visually aligned during the connection procedure, the circuit board 17 of the head board 14 of the present invention can be manufactured so that the two halves of the subminiature connector are visually obscured from the user during the connection procedure, as shown in FIG. 4. By eliminating the requirement for visual observation of the two halves of the electrical connector during the connection process, the present invention may be manufactured so as to be advantageously positioned closer to the top of the head of a research animal than prior art devices.

In addition to the advantageous head positioning of the present invention over the prior art, the present invention also comprises an improved electrical connector assembly. In the prior art, the pins of the top pin connector must be manually inserted into the socket of the top socket connector to a depth of about 2.2 millimeters (mm), with an insertion force of about three pounds (lbs). By contrast, the pins (male contacts) of the magnetically-assisted subminiature connector are manually inserted into the socket to a depth of only about 0.2 mm, with an insertion force of also about three lbs. This means that the energy required to make the electrical connection between the EIB and the head stage of the present invention is only about 9% of the energy required to make the equivalent connection with the prior art device. Because much of the connection energy is transmitted to the head of the test animal during the connection procedure, a reduction in the connection force causes less trauma to the animal. Furthermore, because the attractive force of the magnets of the present invention helps pull the two halves of the connector together, the downward pressure that is exerted on the head of the animal during the connection process is reduced.

The disconnection process of the present invention requires much less upward force on the head of the animal than is produced when disconnecting the EIB and the head stage of the prior art. Because the electrical connector of the present invention relies primarily on magnetic attraction rather than high frictional forces between the contact pins to keep the EIB and head stage connected, the disconnect pull force on the implant harness is significantly reduced compared to the prior art, causing less stress to the animal and reducing the chance of equipment damage. To detach the connection of the present invention, the user places a thumb on one edge of the space between the EIB and the head stage circuit boards and a finger on the other side. The head stage is rocked to one side, which breaks the hold of the magnets on the opposite side of the circuit boards. This leaves the head board attached to the EIB on one side by one set of weakly attached magnets, and the head board can then be pulled away from the EIB with a lateral motion. Neither the rocking motion nor lateral pulling motion of the disconnection process requires downward force to be applied to the top of the animal's head.

The subminiature pins of the plug and socket components of the connector of the present invention are manufactured so as to be protected by physical components of the invention (in the case of the male contacts, by the magnets, and in the case of the female contacts, by the molded plastic housing of the socket portion), whereas the pins of the prior art connector are exposed. For this reason, in contrast to the prior art, the connector pins of the present invention are not subject to damage by accidental contact due to misalignment or other handling errors. The details of the improved electrical connector are described, in reference to the following FIG. 5 through 9.

Figure 5:
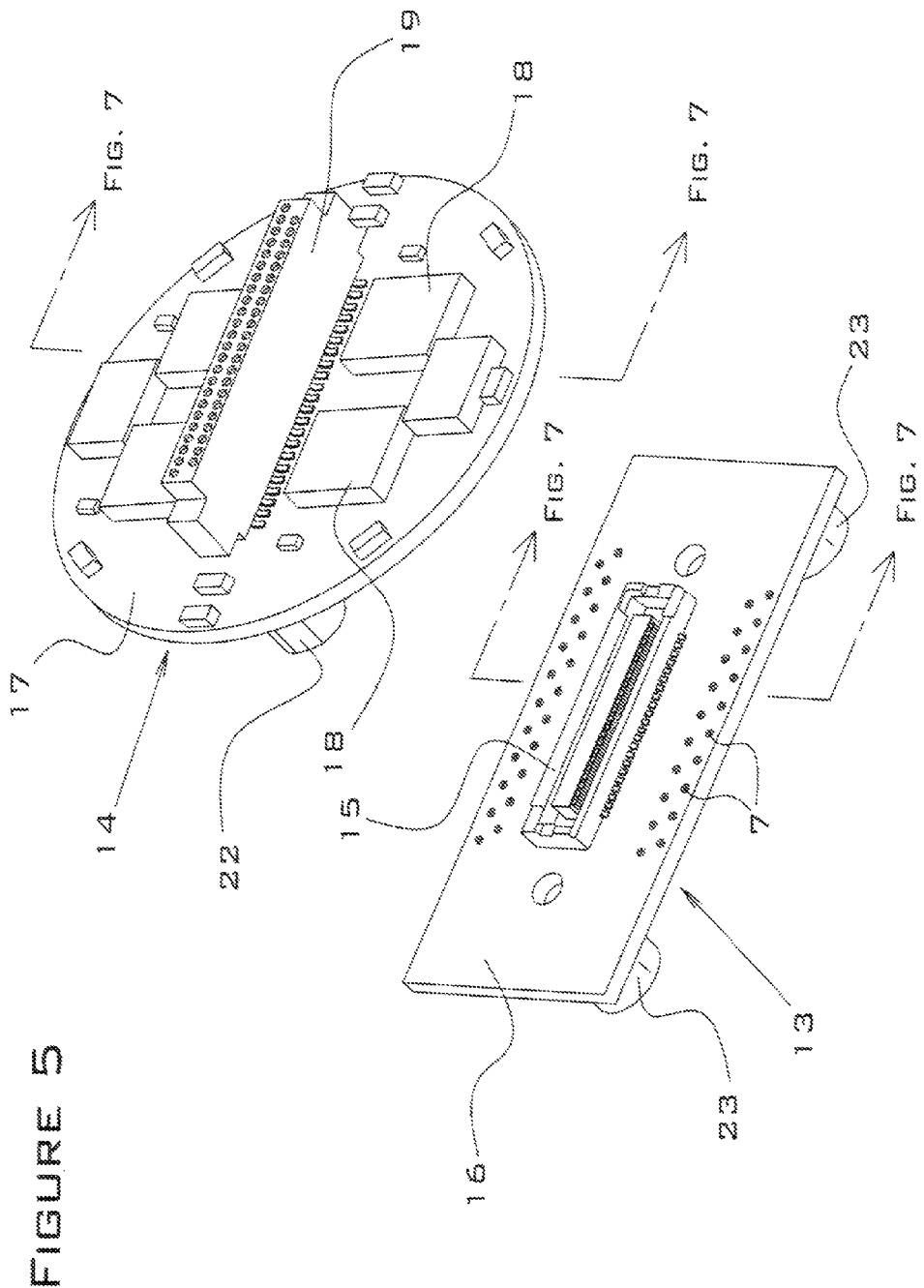
FIG. 5 is a magnified perspective view of the top sides of the EIB and the head stage of the present invention, shown disconnected.

FIGS. 5 and 6 are magnified perspective views of the top and bottom sides, respectively, of the EIB 13 and the head stage 14 of the present invention, shown disconnected. FIG. 5 shows the socket portion of the subminiature dual-row connector 15 soldered to the top surface of the circuit board 16 of the EIB 13. One example of a suitable subminiature connector socket is the Molex 44 Pin Socket #51338-4473 manufactured by the Molex Corporation of Lisle, Ill. Also shown on the EIB 13 are the electrode connection solder holes 7 said two of the four EIB magnets 23 that are attached to the bottom of the circuit board 16.

Components mounted on the top surface of the of the head stage 14 shown in FIG. 5 include a plurality of analog-to-digital integrated circuit chips 18 and the top socket connector 19. One example of a suitable top socket connector is the Omnetics 1348 dual-row connector manufactured by Omnetics Connector Corporation of Minneapolis, Minn.

FIG. 6 shows the plug portion 24 of the subminiature dual-row connector that is mounted on the bottom surface of the circuit board 17 of the head stage 14. One example of a suitable subminiature dual-row connector plug is the Molex 44 Pin Plug #55909-4472 manufactured by the Molex Corporation of Lisle, Ill. The plug 24 mates with the socket 15 shown in FIG. 5. As previously described, the electrical contacts of the plug 24 are connected to the electrical contacts of the top socket connector 19 (shown in FIG. 5) that is mounted on the top side of the circuit board 17.

Also shown in FIG. 6 are the four EIB magnets 23 that are attached to the bottom surface of the circuit board 16 of the EIB 13 and the four head-stage magnets 22 that are attached to the bottom surface of the circuit board 17 of the head stage 14. The letters "N" and "S" shown on the magnets 22, 23 illustrate the polarity orientation of each of the magnets 22, 23. With the magnet polarities as shown, the four EIB magnets 23 are attracted to the four head-stage magnets 22; however, if the EIB 13 were inadvertently rotated 180 degrees with respect to the head stage 14 during a connection procedure, the four EIB magnets 23 would be repelled by the four head-stage magnets 22, thereby preventing the plug 24 and the socket 15 (shown in FIG. 5) from being incorrectly connected. In a preferred embodiment, the eight magnets 22, 23 are identical and are cylindrical in shape, with a diameter of approximately 3.4 mm and a height of approximately 1.5 mm. The magnets 22, 23 are preferably comprised of rare earth metals and are attached to the circuit boards 16, 17 with an epoxy adhesive.

Figure 7:
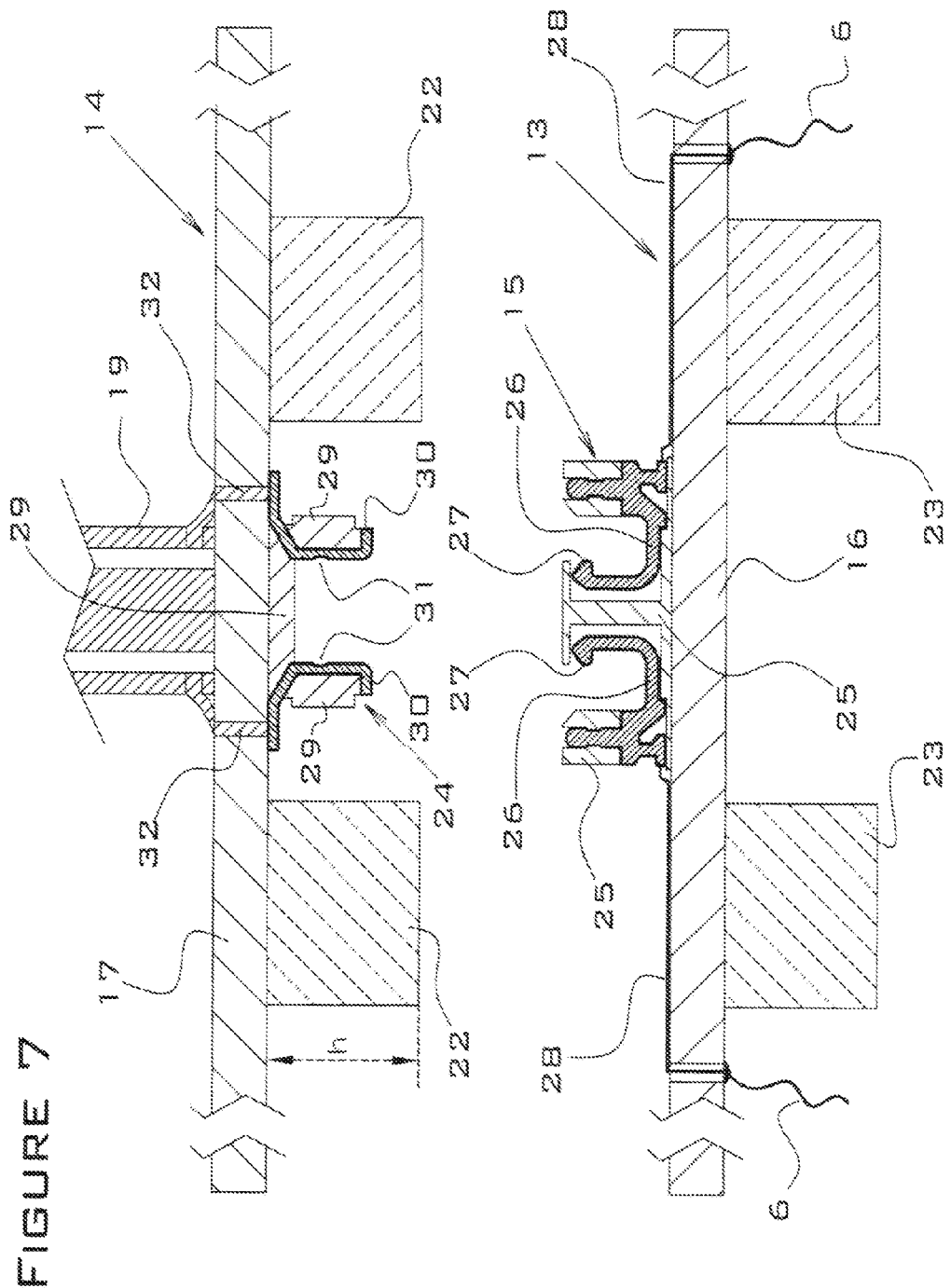
FIG. 7 is a magnified cross-section view of the EIB and the head stage illustrating the relative vertical orientation of these components prior to connection.

FIG. 7 through 11 illustrate the details of the magnetically-assisted connection, components and the connection procedure of the present invention. FIG. 7 shows magnified cross-section views of the EIB 13 and the head stage 14 taken at the section lines shown in FIG. 5, illustrating the EIB 13 and the head stage 14 disconnected but in vertical alignment. As previously described, the EIB 13 comprises a circuit board 16 that has magnets 23 mounted on the lower surface and a socket portion 15 of a subminiature connector mounted on the top surface. The socket 15 is attached to the printed circuit board 16 via surface-mount soldering. The socket 15 comprises a molded plastic housing 25 and a plurality of metallic female contacts 26, two of which are shown. As shown in this figure, the female contacts 26 are recessed into the plastic housing 25.

Each female contact 26 has a protruding contact point 27. Each of the female contacts 26 is connected to an electrode wire 6 via a circuit board conductor 28. The head stage 14 comprises a printed circuit board 17 with magnets 22 mounted on the bottom surface. The height "b" shown, measured from the bottom of the circuit board 17 to the bottom of each magnet 22, is a critical dimension that is explained in more detail in reference to the following FIGS. 10 and 11. As shown in FIG. 7, the plug portion 24 of the subminiature dual-row connector is mounted on the bottom surface of the head stage circuit board 17 and is attached via surface-mount soldering. The plug 24 comprises a molded plastic housing 29 and a plurality of metallic male contacts 30, two of which are shown. Each male contact 30 comprises a detent 31 that is described in more detail in reference to the following FIG. 10 through 14. Each male contact 30 is electrically connected to a contact in the top socket connector 19 via a through-board connection 32.

Figure 8:
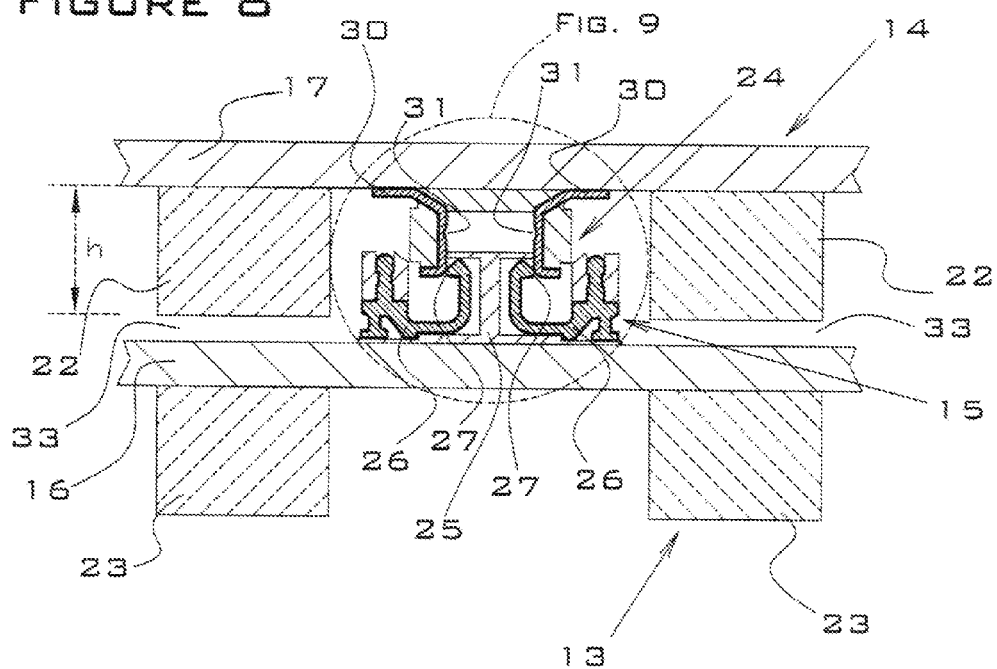
FIG. 8 is a simplified partial cross-section view of the EIB and the head stage illustrating the relative vertical orientation of these components after step 1 of the connection procedure.
Figure 9:
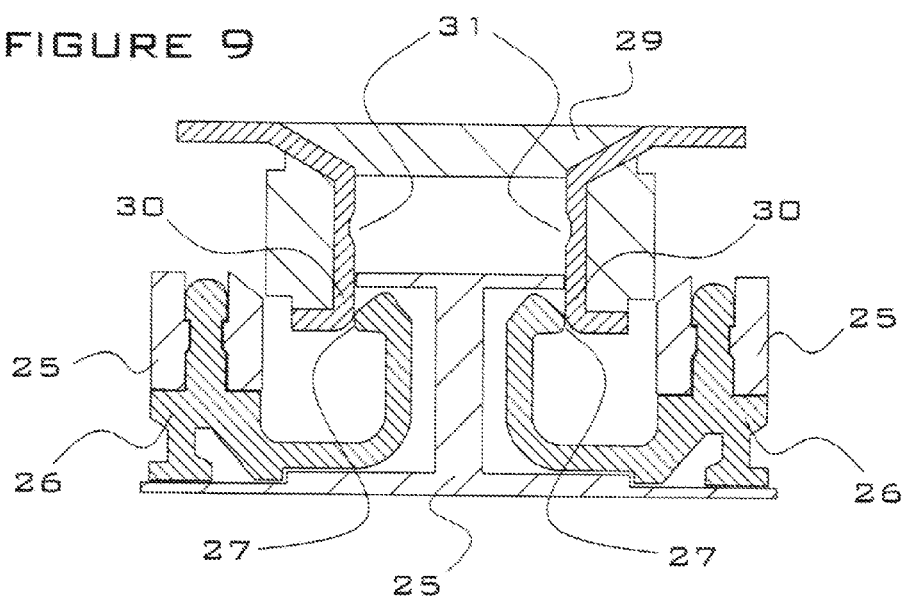
FIG. 9 is magnified view of the electrical contacts shown in FIG. 8.

FIG. 8 is a simplified partial cross-section view of the EIB 13 and the head stage 14 shown in FIG. 7, with the top socket connector 19 and electrode wiring 6 removed for clarity, and the female contacts 26 touching the male contacts 30. FIG. 9 is a magnified detail view of the male and female electrical contacts shown in FIG. 8. FIG. 8 through 11 illustrate a key feature of the present invention, which is the sequence that provides a magnetically aligned and attached connection of the socket 15 with the plug 24 of the subminiature connector. As previously described, the connection procedure involves two sequential steps. In step 1, the EIB 13 and the head stage 14 are manually brought into approximate alignment, at which point the attractive magnetic force between the magnets 22, 23 in the two components 13, 14 bring the two components into precise alignment. FIGS. 8 and 9 illustrate the relative positions of the EIB 13 and the head stage 14 at the end of step 1, when the magnets 22, 23 have pulled components of the EIB 13 and the head board 14 into physical contact. At this point, the contact point 27 of each female contact 26 is touching the surface (specifically, the inside distal end) of its mating male contact 30, and friction between the parts 20, 30 prevents the magnetic attractive force of the magnets 22, 23 from further seating the male contacts 30 into their corresponding female contacts 26. In this position, a gap 33 exists between the bottom of each magnet 22 and the top surface of the EIB circuit board 16, as shown in FIG. 8. In a preferred embodiment, the height of the gap 33 is about 0.2 mm. Note that this gap 33 is eliminated upon completion of step 2, described below.

Figure 10:
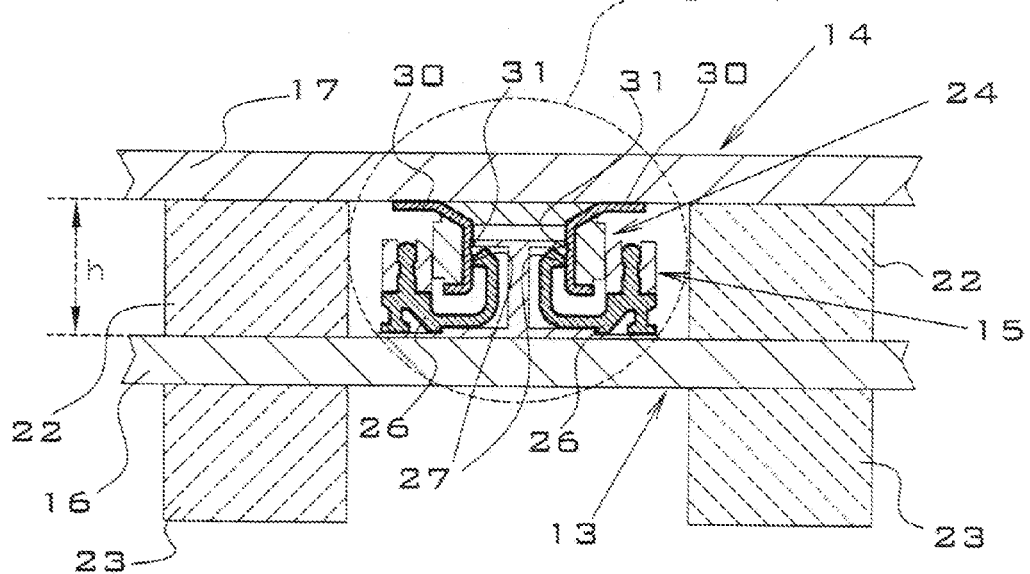
FIG. 10 is a simplified partial cross-section view of the EIB and the head stage illustrating the relative vertical orientation of these components after step 2 of the connection procedure.
Figure 11:
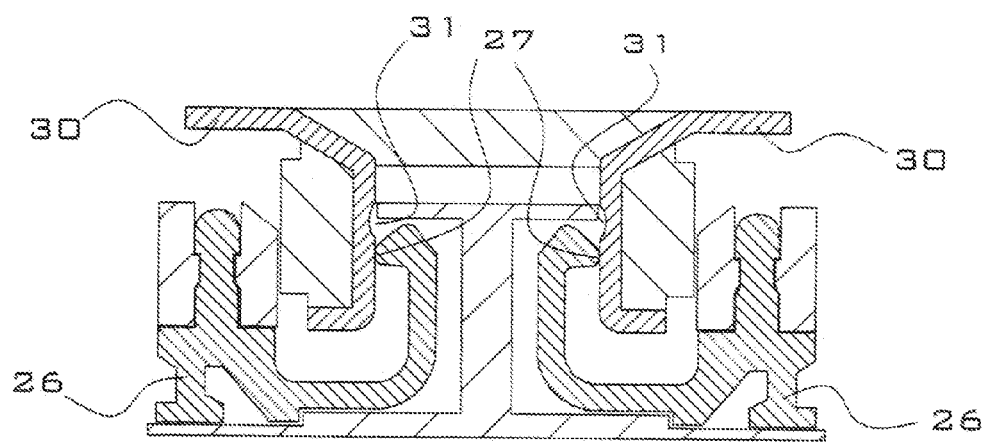
FIG. 11 is a magnified view of the electrical contacts shown in FIG. 10.

FIG. 10 is a simplified partial cross-section view of the EIB 13 and the head stage 14 shown in FIG. 7, with the top socket connector 10 and electrode wiring 6 removed for clarity. FIG. 11 is a magnified detail view of the male and female electrical contacts shown in FIG. 10. FIGS. 10 and 11 are similar to FIGS. 8 and 9, except that the connector parts are shown in their respective positions after step 2 of the connection procedure has been completed. To perform step 2 of the connection procedure, after the EIB 13 and head stage 14 are positioned as shown in FIG. 8, manual pressure is applied by the user to the two parts, for example, by gently squeezing the parts together with compressive force applied by the fingers. When the user applies sufficient force, the two parts will snap together until the head-stage magnets 22 butt up against the top surface of the EIB circuit board 16 as shown in FIG. 10. Note that the gap 33 has been eliminated.

In the position shown in FIG. 10, the plug 24 and the socket 15 are fully connected according to the design of the present invention, although the contact points 27 of the female contacts 26 have not moved sufficiently to engage the detents 31 of the male contacts 30, as shown most clearly in FIG. 11. Further travel of the female contacts 26 is prevented by the position of the head-stage magnets 22 against the top of the EIB circuit board 16. The height "h" of the magnets below the head stage circuit board 17 is precisely set during manufacture of the head stage 14 so that the contact points 27 of the female contacts 26 travel far enough to make good contact with the male contacts 30 but do not travel far enough to snap into the detents 31 of the male contacts 30. Once the connection has been made as shown, the attractive magnetic force provided by the magnets 22, 23 prevents the plug 24 and the socket 15 from becoming accidently disconnected.

Figure 12:
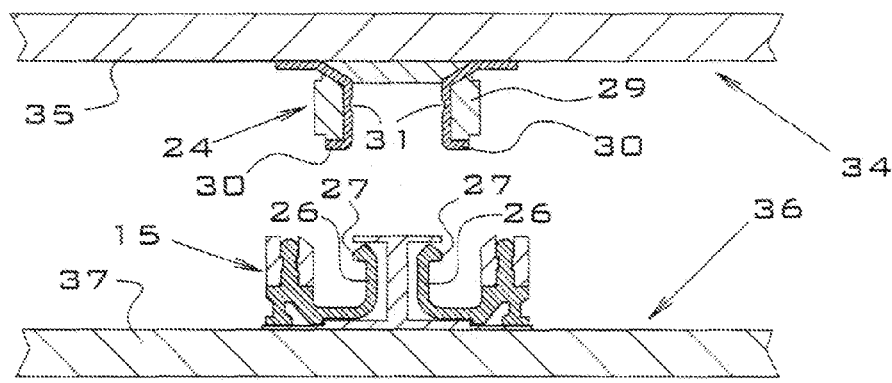
FIG. 12 is a magnified cross-section view of the same subminiature electrical connector as in the present invention, but used in a "standard" or prior art connection configuration, shown with the two halves of the connector disconnected.
Figure 13:
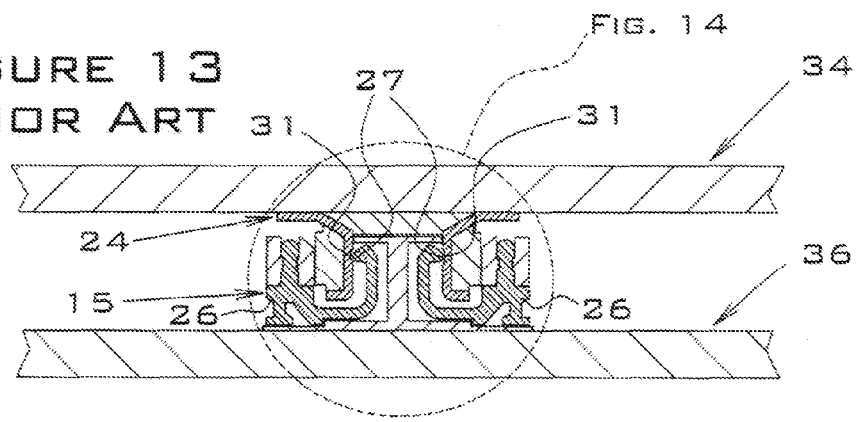
FIG. 13 is a magnified cross-section view of the same subminiature electrical connector as in the present invention, hot used, in a "standard" or prior art connection configuration, shown with the two halves of the connector electrically connected.
Figure 14:
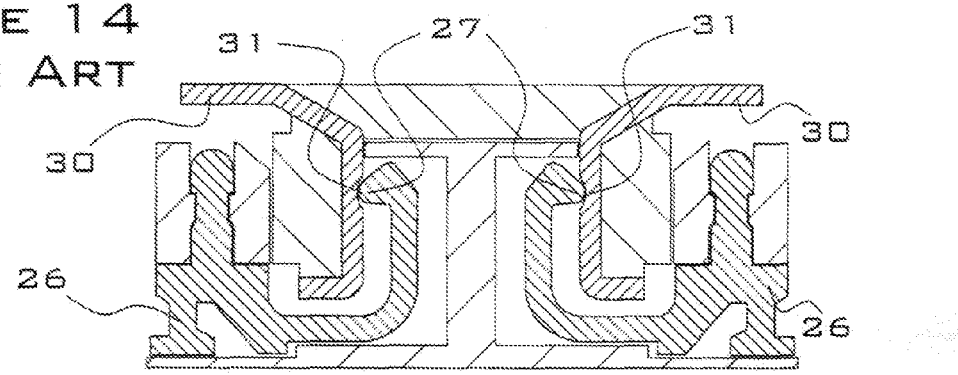
FIG. 14 is a magnified view of the electrical contacts shown in FIG. 13.

FIG. 12 through 14 show a standard, prior art method of connecting the two halves of the same subminiature dual-row connector that is used in the present invention. These figures illustrate the differences between positions of the connection components when the connector is utilized in a standard application as compared to the positions of the connection components when the connector is used in the magnetically-assisted connection configuration of the present invention, as shown previously in FIG. 8 through 11.

FIG. 12 is a cross-section view of an upper circuit board assembly 34 composing a top printed circuit board 35 and a plug portion 24 of a subminiature dual-row corrector, and a lower circuit board assembly 36 comprising a bottom printed circuit board 37 and a socket portion 15 of a subminiature dual-row connector. The subminiature connector plug 24 and socket 15 are the same components as those incorporated within the present invention and shown in the previous FIG. 3 through 11. The two circuit board assemblies 34, 36 are shown in FIG. 12 with the plug 24 and socket 15 spatially and electrically separated, prior to being connected.

FIG. 13 is a cross-section view of the components shown in FIG. 12, with the plug 24 and the socket 15 shown in a standard (prior art) fully connected position, as would occur when the circuit board assemblies 34, 36 are pushed together with the plug 24 and the socket 15 in proper alignment. FIG. 14 is a magnified view of the electrical contacts 26, 32 shown in FIG. 13. As shown in FIGS. 13 and 14, because there is no magnet or other external object to serve as a stop to limit the full engagement of the two connector components 24, 15, the protruding contact point 27 of each female contact 26 travels sufficiently so as to snap into and engage the detent 31 of the mating male contact 30.

For the prior art shown in FIG. 12 through 14, manual force is required to snap the female contacts 26 into the detents 31 during the connection process. For the present invention, during the connection process, a combination of magnetic attractive force and manual force is used to slide the female contacts 26 into contact with the male contacts 30. With the present invention, because the female contacts 26 do not engage the detents 31, no force is required to snap the contacts into the detents. With the present invention, due to the magnetic assisting force available and also due to the fact that the female contacts are not engaged into detents, the manual force required to make a reliable electrical and physical connection of the subminiature connector is significantly less than the manual force required to make a reliable connection in the prior art shown in FIG. 12 through 14.

In the prior art, in order to disconnect the two halves of the subminiature connector, significant force is required in snap the female contacts out of the detents. In the present invention, this force requirement is eliminated because the contacts are not engaged in the detents, and the manual force required to disconnect the two halves of the connector is equal to the force required to overcome the magnetic attractive force plus the force required to overcome the sliding friction of the female contacts along the male contacts. By adjusting the attractive magnetic force of the magnets, the present invention can be designed to require less force to disconnect the connector than is required in the prior art. This is an important advantage of the present invention because the head stage of the present invention can be designed to disconnect from the EIB at a force less than a damaging force to the animal.

The connection mechanism of the present invention shown in FIG. 8 through 11 is designed to have an operational lifetime of over 1000 connect/disconnect cycles, whereas the subminiature connector shown in FIG. 12 through 14 has an expected lifetime of only 50 cycles, due primarily to the friction wear on the contacts that occurs when the female contacts are snapped into and out of the detents of the male contacts. The extended lifetime of the present invention compared to the lifetime of the prior art shown in FIG. 12 through 14 provides yet another important advantage of the present invention over this prior art.

Although the present invention has been described for use in conjunction with laboratory rats, it is also suitable for use with other animals, including humans. For example, the present invention may be used as a neural monitor for the analysis and treatment of human patients afflicted with epilepsy or Parkinson's disease.

Although the present invention has been described for use with 44-contact connectors, it is suitable for use with connectors having fewer or greater contacts, for example, connectors having 36 to 90 contacts. Although the present invention has been described as comprising a single subminiature connector, the magnetically aligned and attached components and procedures of the present invention may be used in conjunction with multiple subminiature connectors.

Although the preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An electrical connector assembly for a neural monitoring device, the electrical connector assembly comprising:
    (a) an electrode interface board comprising a first printed circuit board with a top surface and a bottom surface, wherein a socket portion of a subminiature dual-row electrical connector is attached to the top surface of the first printed circuit board, wherein a first plurality of magnets is attached to the bottom surface of the first printed circuit board, and wherein the socket portion comprises a plastic housing and a plurality of female contacts, each female contact comprising a protruding contact point; and
    (b) a head stage comprising a top socket connector and a second printed circuit board with a top surface and a bottom surface, wherein a plug portion of a subminiature dual-row electrical connector is attached to the bottom surface of the second printed circuit board, wherein a second plurality of magnets is attached to the bottom surface of the second printed circuit board, wherein each magnet has a height, wherein the height of all of the magnets in the second plurality of magnets is the same, wherein the plug portion comprises a plastic housing and a plurality of male contacts, each male contact comprising a detent, and wherein each of the male contacts in the plurality of male contacts is electrically connected to the top socket connector via a through-board connection;
    wherein the male contacts of the plug portion mate with the female contacts of the socket portion so that the protruding contact point of each female contact touches an inside distal surface of a male contact, and wherein the height of the magnets in the second plurality of magnets prevents the male contacts from seating further into the female contacts; wherein the protruding contact point of each female contact does not travel far enough to snap into the detent of the male contact.

2. The electrical connector assembly of claim 1, wherein the protruding contact point of each of the female contacts in the plurality of female contacts does not engage with the detent of the male contact but stops short of the detent as a result of the configuration and height of the magnets in the second plurality of magnets.

3. The electrical connector assembly of claim 1, wherein the magnets in the first plurality of magnets and the magnets in the second plurality of magnets are configured so as to cause the male contacts of the plug portion of the head stage to align precisely over the female contacts of the socket portion of the electrode interface board when the head stage and electrode interface board are brought into approximate alignment.

4. The electrical connector assembly of claim 1, wherein the magnets in the first plurality of magnets and the magnets in the second plurality of magnets are configured so as to cause the electrode interface board and the head stage to be magnetically repelled if they are brought into reverse alignment.

5. The electrical connector assembly of claim 1, wherein the female contacts are recessed into the plastic housing of the socket portion.

6. A method for attaching an electrode interface board to a head stage of a neural monitoring device for use in experiments on live animals, the method comprising the steps of:
    (a) wherein the electrode interface board comprises a first printed circuit board with a top surface and a bottom surface, attaching a socket portion of a subminiature dual-row electrical connector to the top surface of the first printed circuit board, the socket portion comprising a plurality of female contacts, and attaching a first plurality of magnets to the bottom surface of the first printed circuit board;
    (b) wherein the head stage comprises a second printed circuit board with a bottom surface, attaching a plug portion of a subminiature dual-row electrical connector to the bottom surface of the second printed circuit board, the plug portion comprising a plurality of male contacts, and attaching a second plurality of magnets to the bottom surface of the second printed circuit board, each magnet in the second plurality of magnets having a bottom surface;
    (c) using the first plurality of magnets and the second plurality of magnets to align the female contacts with the male contacts to create a gap of roughly 0.2 millimeters between the bottom surface of each magnet in the second plurality of magnets and the top surface of the first printed circuit board; and (d) closing the gap between the bottom surface of each magnet in the second plurality of magnets and the top surface of the first printed circuit board by manually pressing the male contacts into the female contacts until the bottom surface of the magnets in the second plurality of magnets comes into contact with the top surface of the printed circuit board.

* * * * *